(12) United States Patent
Ferzli

(10) Patent No.: US 10,912,539 B2
(45) Date of Patent: Feb. 9, 2021

(54) ENDOSWAB FOR SAMPLING AND CULTURE IN MINIMALLY INVASIVE SURGERY

(71) Applicant: New York University, New York, NY (US)

(72) Inventor: George S. Ferzli, Staten Island, NY (US)

(73) Assignee: New York University, New York, NY (US)

( * ) Notice: Subject to any disclaimer, the term of this patent is extended or adjusted under 35 U.S.C. 154(b) by 431 days.

(21) Appl. No.: 15/888,750

(22) Filed: Feb. 5, 2018

(65) Prior Publication Data

US 2018/0220999 A1    Aug. 9, 2018

Related U.S. Application Data

(60) Provisional application No. 62/455,939, filed on Feb. 7, 2017.

(51) Int. Cl.
*A61B 5/00* (2006.01)
*A61B 10/00* (2006.01)
(Continued)

(52) U.S. Cl.
CPC .......... *A61B 10/0045* (2013.01); *A61B 10/02* (2013.01); *C12M 23/06* (2013.01);
(Continued)

(58) Field of Classification Search
CPC ....... A61K 9/0019; A61K 38/00; A61P 17/02; A61P 43/00; A61P 19/02; A61P 1/00; A61B 17/32053; A61B 17/32093; A61B 17/322; A61B 2017/2215; A61B 10/02; A61B 17/00234; A61B 17/24; A61B 2018/00601; A61B 10/0045; A61B 1/303
(Continued)

(56) References Cited

U.S. PATENT DOCUMENTS 3,939,822 A * 2/1976 Markowitz ........ A61B 5/15003
600/575
3,960,139 A * 6/1976 Bailey ................ A61B 5/15003
600/575
(Continued)

*Primary Examiner* — May A Abouelela
(74) *Attorney, Agent, or Firm* — Fay Kaplun & Marcin, LLP

(57) ABSTRACT

A medical device includes a hollow shaft, a hollow housing, and a syringe. The syringe has a housing defining a fluid receiving chamber and a plunger slidably received therein. The shaft extending distally from the plunger and exiting the syringe via a distal opening therein. A proximal portion of the shaft includes a first opening permitting fluid flow from a central lumen of the shaft to an exterior thereof. The first opening is located on the shaft so that the first opening remains within the syringe through an entire range of motion of the plunger. A distal end of the shaft is surrounded by an absorbent material. The hollow housing extends distally from the syringe and surrounding the shaft. The housing is sized so that, when the plunger is withdrawn to a proximal-most position, the distal end is received within the housing and, when the plunger is advanced distally through the syringe, the distal end is extended distally out of a distal opening in the housing.

22 Claims, 2 Drawing Sheets

(51) Int. Cl.
*C12M 1/00* (2006.01)
*C12M 1/12* (2006.01)
*A61B 10/02* (2006.01)
*C12M 1/30* (2006.01)

(52) U.S. Cl.
CPC ............ *C12M 23/20* (2013.01); *C12M 25/14* (2013.01); *C12M 33/02* (2013.01); *A61B 2010/0216* (2013.01)

(58) Field of Classification Search
USPC .......... 600/300, 573–584, 591; 604/143, 198
See application file for complete search history.

(56) References Cited

U.S. PATENT DOCUMENTS

| | | | | | |
|---|---|---|---|---|---|
| 4,036,232 | A * | 7/1977 | Genese | ............... | A61M 1/0009 604/143 |
| 4,105,500 | A * | 8/1978 | Libman | ............ | B01L 3/502 435/30 |
| 4,245,655 | A * | 1/1981 | Patel | ............. | A61B 5/15003 600/578 |
| 4,266,558 | A * | 5/1981 | Akhavi | ............ | A61B 5/150305 600/579 |
| 4,595,021 | A * | 6/1986 | Shimizu | ............. | A61B 5/15003 600/578 |
| 4,684,366 | A * | 8/1987 | Denny | .................. | F42B 12/54 43/43.13 |
| 4,687,001 | A * | 8/1987 | Arko | ................... | A61B 10/02 600/580 |
| 4,732,162 | A * | 3/1988 | Martell | ............. | A61B 5/15003 600/578 |
| 4,744,786 | A * | 5/1988 | Hooven | ............... | A61M 5/155 128/DIG. 12 |
| 4,790,824 | A * | 12/1988 | Morrow | .................. | A61M 5/30 604/143 |
| 4,815,477 | A * | 3/1989 | McWhorter | .......... | A61B 10/007 251/4 |
| 4,877,037 | A * | 10/1989 | Ko | .......................... | A61B 17/34 600/569 |
| 4,917,679 | A * | 4/1990 | Kronner | ............. | A61M 5/3271 600/576 |
| 4,936,315 | A * | 6/1990 | Lineback | ........... | A61B 5/15003 600/578 |
| 4,944,726 | A * | 7/1990 | Hilal | ..................... | A61M 5/007 222/389 |
| 5,015,237 | A * | 5/1991 | Kleinwolterink, Jr. ................... A61D 1/025 604/141 | | |
| 5,086,783 | A * | 2/1992 | Macors | ............. | A61M 5/31511 600/578 |
| 5,147,329 | A * | 9/1992 | Brannon | ........... | A61B 5/15003 600/577 |
| 5,193,552 | A * | 3/1993 | Columbus | ........ | A61B 5/150916 422/918 |
| 5,267,973 | A * | 12/1993 | Haber | .................... | A61M 5/322 600/578 |
| 5,295,971 | A * | 3/1994 | Cameron | ............ | A61M 5/3287 473/581 |
| 5,304,128 | A * | 4/1994 | Haber | ................. | A61M 5/2046 604/143 |
| 5,374,250 | A * | 12/1994 | Dixon | .................. | A61M 5/322 600/576 |
| 5,429,610 | A * | 7/1995 | Vaillancourt | ..... | A61M 5/31596 600/573 |
| 5,520,657 | A * | 5/1996 | Sellers | .................. | A61M 25/06 600/575 |
| 5,769,824 | A * | 6/1998 | Hjertman | .......... | A61M 5/14526 604/143 |
| 5,807,344 | A * | 9/1998 | Iwasaki | ............. | A61B 5/15003 600/576 |
| 5,810,778 | A * | 9/1998 | Hjertman | .......... | A61M 5/1454 604/143 |
| 5,891,052 | A * | 4/1999 | Simmons | ........... | A61B 10/0283 600/573 |
| 6,139,530 | A * | 10/2000 | Hiejima | ........... | A61M 5/14526 604/140 |
| 6,485,428 | B1 * | 11/2002 | Enk | ....................... | A61B 5/0215 600/485 |
| 6,511,439 | B1 * | 1/2003 | Tabata | ............... | A61B 5/15003 600/573 |
| 6,537,257 | B1 * | 3/2003 | Wien | ................... | A61M 5/3202 604/198 |
| 6,830,560 | B1 * | 12/2004 | Gross | .................. | A61M 5/2046 604/143 |
| 6,890,320 | B2 * | 5/2005 | Minezaki | .......... | A61M 5/14526 604/140 |
| 6,911,021 | B2 * | 6/2005 | Yang | .................. | A61B 5/15003 600/575 |
| 7,207,951 | B1 * | 4/2007 | Lurie | ................. | A61B 10/0045 600/578 |
| 7,662,110 | B2 * | 2/2010 | Flaherty | .............. | A61M 5/1407 600/486 |
| 7,927,630 | B2 * | 4/2011 | Johnson | .................. | A61K 47/46 424/537 |
| 8,808,202 | B2 * | 8/2014 | Brancazio | ............ | A61B 5/1411 600/583 |
| 2002/0111565 | A1 * | 8/2002 | Roe | .................... | A61B 5/15117 600/578 |
| 2007/0244368 | A1 * | 10/2007 | Bayloff | ................. | G01N 1/02 600/300 |
| 2012/0022404 | A1 * | 1/2012 | Fojtik | ............... | A61B 5/150259 600/578 |
| 2012/0316467 | A1 * | 12/2012 | Kolb | ................ | A61B 5/150404 600/578 |
| 2012/0323142 | A1 * | 12/2012 | Allen et al. | ....... | A61B 5/150496 600/576 |
| 2013/0079599 | A1 * | 3/2013 | Holmes | ................ | A61B 5/0002 600/300 |
| 2013/0172779 | A1 * | 7/2013 | Spearman | ........ | A61B 5/150503 600/578 |
| 2013/0281927 | A1 * | 10/2013 | Jennings | ............. | A61M 5/2053 604/143 |
| 2014/0128775 | A1 * | 5/2014 | Andreae | ............. | A61B 5/1405 600/581 |
| 2014/0163419 | A1 * | 6/2014 | Bullington | ........... | A61B 5/1416 600/575 |
| 2014/0330204 | A1 * | 11/2014 | Huculak | ............. | A61M 5/2046 604/143 |
| 2015/0087944 | A1 * | 3/2015 | Levinson | ........... | A61B 5/15125 600/365 |
| 2015/0144127 | A1 * | 5/2015 | Ekman | ................ | A61M 11/065 128/200.14 |
| 2015/0151045 | A1 * | 6/2015 | Anderson | ............ | A61M 5/155 604/143 |
| 2015/0272492 | A1 * | 10/2015 | Schraga | ........... | A61B 5/150603 600/578 |
| 2015/0328405 | A1 * | 11/2015 | Metzner | ............... | A61M 5/2046 604/143 |
| 2016/0100786 | A1 * | 4/2016 | Nishio | ............. | A61B 5/150755 600/578 |
| 2016/0135724 | A1 * | 5/2016 | Bullington | ....... | A61B 5/150236 600/575 |
| 2016/0174948 | A1 * | 6/2016 | Kato | ................ | A61B 5/150358 600/580 |

* cited by examiner

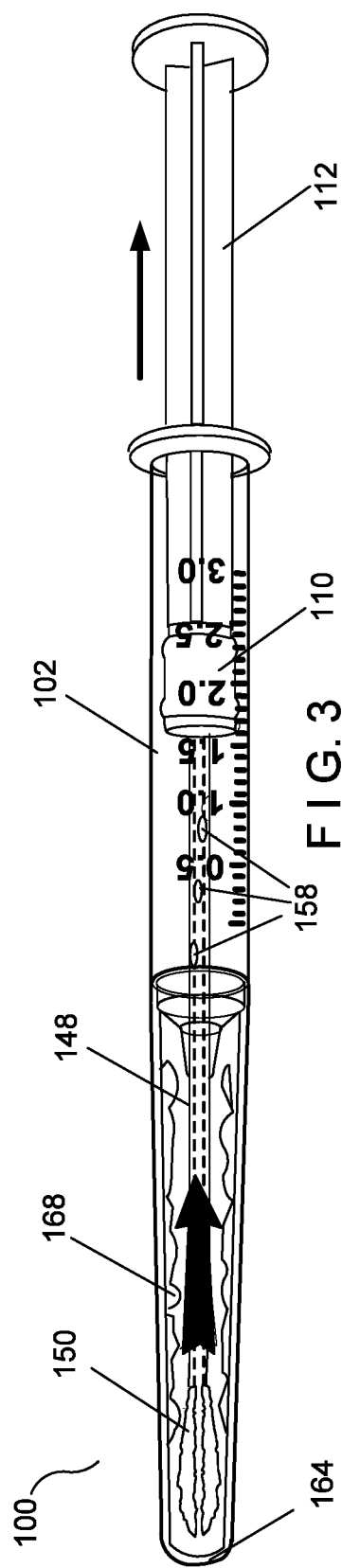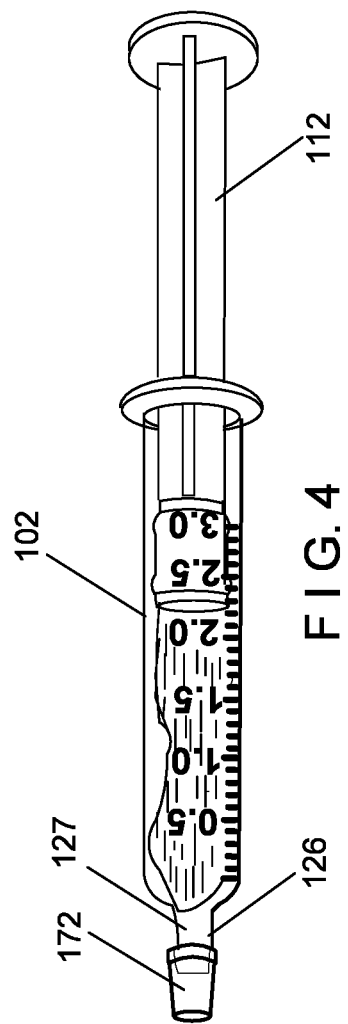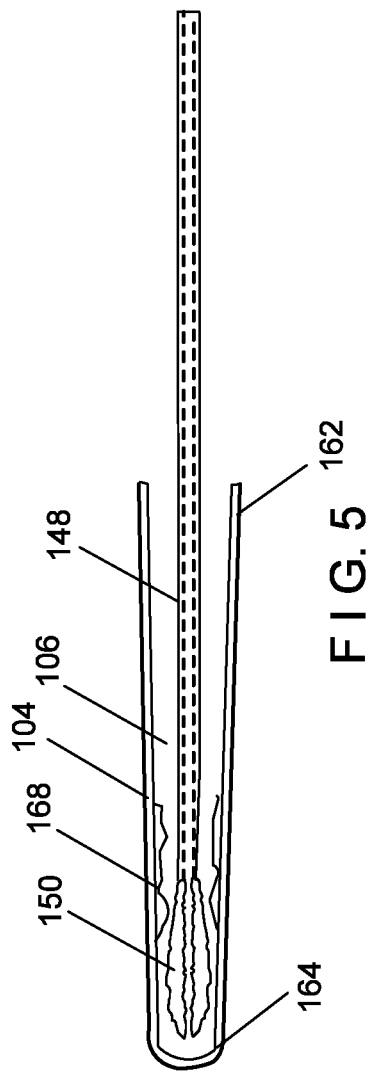

ENDOSWAB FOR SAMPLING AND CULTURE IN MINIMALLY INVASIVE SURGERY

PRIORITY CLAIM

The present disclosure claims priority to U.S. Provisional Patent Application Ser. No. 62/455,939 filed Feb. 7, 2017; the disclosure of which is incorporated herewith by reference.

BACKGROUND

There are currently few devices specifically designed for fluid sampling for culture and cytology in minimally invasive, abdominal and thoracic surgeries. Currently such fluid sampling is often done by attaching a specimen trap to a suction device. This can be time consuming and requires the efforts of more than one member of the operating team.

SUMMARY

In accordance with the foregoing objectives and others, one embodiment of the present invention provides devices and methods for sampling fluid for culture and cytology in minimally invasive surgery.

In one aspect, a medical device is provided. The device comprises a syringe including a housing defining a fluid receiving chamber and a plunger slidably received therein, a hollow shaft extending distally from the plunger and exiting the syringe via a distal opening therein, a proximal portion of the shaft including a first opening permitting fluid flow from a central lumen of the shaft to an exterior thereof, the first opening being located on the shaft so that the first opening remains within the syringe through an entire range of motion of the plunger, a distal end of the shaft being surrounded by an absorbent material, and a hollow housing extending distally from the syringe and surrounding the shaft, the housing being sized so that, when the plunger is withdrawn to a proximal-most position, the distal end of the shaft is received within the housing and, when the plunger is advanced distally through the syringe, the distal end of the shaft is extended distally out of a distal opening in the housing. In one embodiment, the device includes an end cap removably coupled to the distal end of the housing. In another embodiment, the shaft includes a second opening located on the shaft, the second opening remaining within the syringe through an entire range of motion of the plunger. In another embodiment, inner walls of the housing are coated with a gel culture medium. In a further embodiment, applying a radially inward force to the shaft causes the inner walls of the shaft to contact the absorbent material such that the gel culture medium coats the absorbent material. In another embodiment, the shaft and the distal opening of the syringe form a seal between the syringe and the housing. In another embodiment, the housing is removably coupled to the syringe such that application of a predetermined force disconnects the housing from the syringe.

In another aspect, a fluid sampling device is provided. The device includes a syringe including a housing defining a fluid receiving chamber, a stopper slidably received within the syringe, a plunger extending from a proximal end to a distal end, the proximal end of the plunger coupled to the stopper to slide the stopper relative to the housing, a hollow shaft extending distally from the stopper and exiting the syringe via a distal opening therein, a proximal portion of the shaft including a first opening permitting fluid to flow from a distal opening through a central lumen of the shaft and into the fluid receiving chamber, a distal end of the shaft being surrounded by an absorbent material, and a hollow housing extending distally from the syringe and surrounding the shaft, the housing being sized so that, when the plunger is withdrawn to a proximal-most position, the distal end of the shaft is received within the housing and, when the plunger is advanced distally through the syringe, the distal end of the shaft is extended distally out of a distal opening in the housing. In an embodiment, the first opening is located on the shaft so that the first opening remains within the syringe through an entire range of motion of the plunger. In another embodiment, the shaft includes a second opening located on the shaft, the second opening remaining within the syringe through an entire range of motion of the plunger. In a further embodiment, the inner walls of the housing are coated with a gel culture. In another embodiment, applying a radially inward force to the housing causes inner walls of the shaft to contact the absorbent material such that the gel culture medium coats the absorbent material. In a further embodiment, the housing is removably coupled to the syringe such that application of a predetermined force disconnects the housing from the syringe. In an embodiment, the shaft is removably coupled to the stopper such that application of a predetermined force disconnects the shaft from the stopper.

In another embodiment, a method for sampling fluid is provided. The method includes inserting a fluid sampling device into the body until a distal portion thereof is adjacent to a target fluid to be sampled, the fluid sampling device comprising: a syringe including a housing defining a fluid receiving chamber and a plunger slidably received therein, a hollow shaft extending distally from the plunger and exiting the syringe via a distal opening therein, a proximal portion of the shaft including a first opening permitting fluid flow from a central lumen of the shaft to an exterior thereof, the first opening being located on the shaft so that the first opening remains within the syringe through an entire range of motion of the plunger, a distal end of the shaft being surrounded by an absorbent material, and a hollow housing extending distally from the syringe and surrounding the shaft, the housing being sized so that, when the plunger is withdrawn to a proximal-most position, the distal end of the shaft is received within the housing and, when the plunger is advanced distally through the syringe, the distal end of the shaft is extended distally out of a distal opening in the housing, advancing the shaft distally out of the housing, through distal movement of the plunger, such that the absorbent material contacts the target fluid, and drawing the shaft proximally into the housing, through proximal movement of the plunger, so that the target fluid is drawn through the central lumen and into the fluid receiving chamber. In one embodiment, the method includes disconnecting the housing from the syringe. In another embodiment, the method includes disconnecting the shaft from the plunger. In an embodiment, the fluid sampling device further comprises an end cap removably coupled to the distal end of the housing. In an embodiment, the shaft and the distal opening of the syringe form a seal between the syringe and the housing. In another embodiment, the inner walls of the housing are coated with a gel culture medium. In a further embodiment, the method includes applying a radially inward force to the housing so an inner wall of the housing contacts the absorbent material so the gel culture coats the absorbent material.

BRIEF DESCRIPTION

FIG. 3 is another partial cross-sectional view of the fluid sampling device of FIG. 1 according to an exemplary embodiment of the invention;

FIG. 4 is a side view of the syringe according to the embodiment of FIG. 1; and

FIG. 5 is a side view of the housing and swabbing element according to the embodiment of FIG. 1.

DETAILED DESCRIPTION

Figure 1:
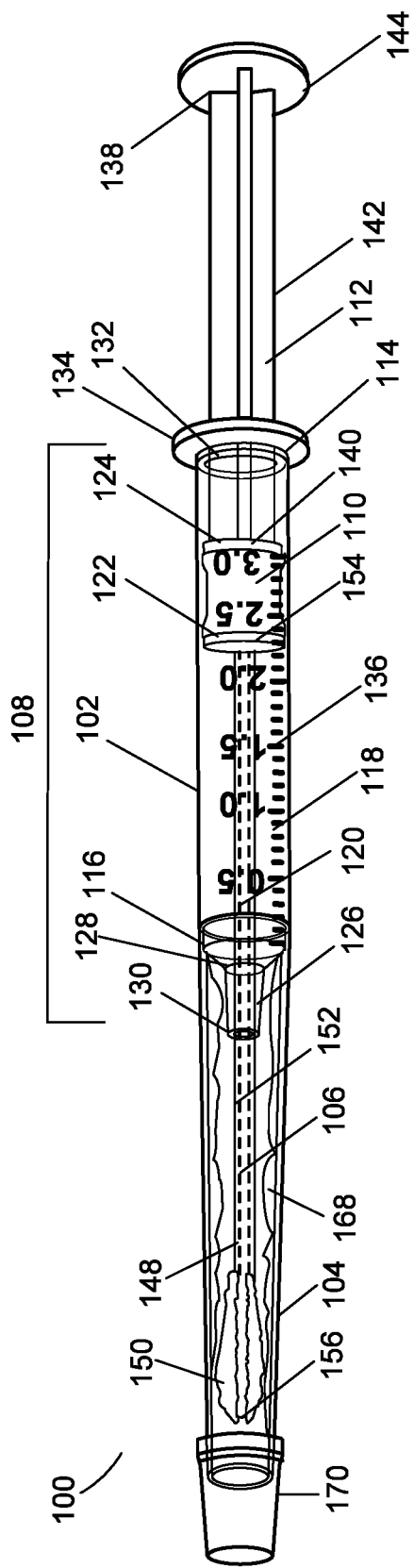
FIG. 1 is a partial cross-sectional view of a fluid sampling device according to an exemplary embodiment of the present invention.

The present embodiments may be further understood with reference to the following description and the appended drawings, wherein like elements are referred to with the same reference numerals. The present embodiments relate generally to methods and devices for sampling fluid for culture and cytology. In particular, the present embodiments relate to methods and devices for swabbing and aspirating a fluid specimen during minimally invasive surgery using a syringe. However, the present embodiments may be employed with any of a plurality of treatment procedures involving cell culture. As used in this application, the terms proximal and distal refer to a direction along the syringe with a first end of the syringe being identified as the proximal end and a second end of the syringe being identified as distal.

Figure 2:
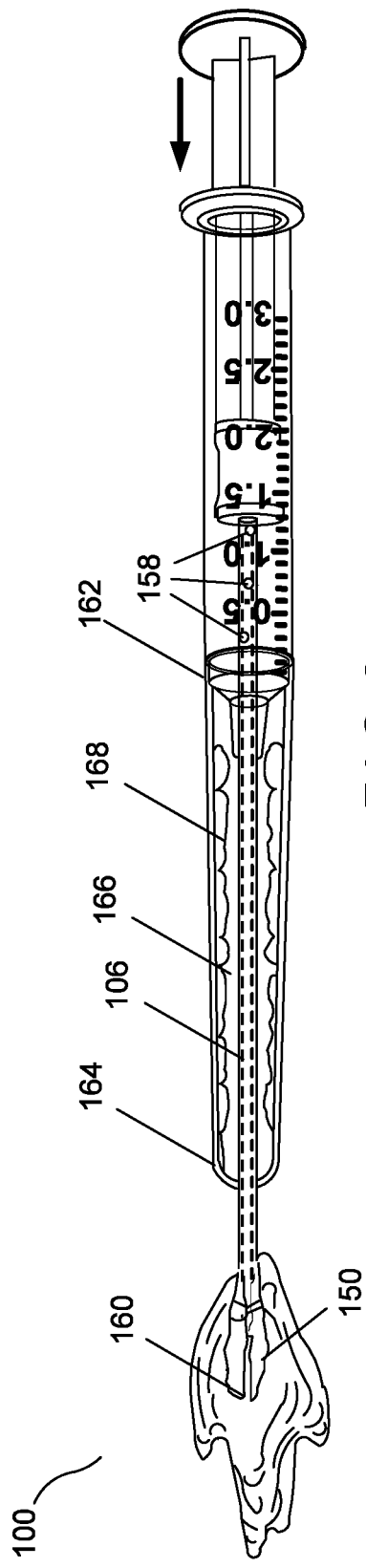
FIG. 2 is another partial cross-sectional view of the fluid sampling device of FIG. 1 according to an exemplary embodiment of the invention.

As shown in FIGS. 1-3, a fluid sampling device 100 according to a first exemplary embodiment comprises a syringe 102, a detachable housing 104 connected to the syringe 102, and a swabbing element 106. The syringe 102 comprises a body 108, a stopper 110 and a plunger 112. The body 108 of the syringe 102 extends from a proximal end 114 to a distal end 116 along a central longitudinal axis L and, in this embodiment, is substantially cylindrical. The body 108 defines a central channel 118 extending therethrough from the proximal end 114 to a reduced diameter nozzle 126 at a distal end 116 of the body 108. In the exemplary embodiment, the central channel 118 has a diameter of approximately 4.5 mm to 30.90 mm and a length of between 65 mm and 450 mm. The stopper 110 is arranged within the body 108 such that a portion of the central channel 118 distal of the distal surface 122 of the stopper 110 defines a fluid receiving chamber 120 the volume of which varies as the stopper 110 moves within the central channel 118. The distal end 116 of the body 108 is formed as a reduced diameter nozzle 126. The nozzle 126 defines a lumen 127 that extends from a proximal opening 128 open to the central channel 118 of the body 108 to a distal opening 130. The nozzle 126 in this embodiment has an outer diameter less than that of a proximal portion of the body 108 and is coupled to the proximal portion of the body 108 by a tapered section. The lumen 127 of this embodiment has a smaller diameter than that of the central channel 118. As would be understood by those skilled in the art, the body 108 may be made from any suitable material, for example a plastic such as polypropylene, polyethylene, polymers, thermoplastics and thermoset plastics or from glass and may include indicia on a surface thereof to act as an aspiration guide. The body 108 may also include a shoulder 132 projecting radially into the central channel 118 at the proximal end 114 to prevent movement of the stopper 110 and plunger 112 proximally out of the central channel 118. The shoulder 132 extends radially into the channel 118 to establish an inner diameter smaller than an outer diameter of the stopper 110 so that the stopper 110 cannot pass proximally beyond the shoulder 132. In an exemplary embodiment, the body 108 also includes a flange 134 projecting radially outward from the body 108 at the proximal end 114 thereof to facilitate user handling of the device 100. As would be understood by those skilled in the art, the flange 134 provides a larger surface area for contact by the user than a bare end of the body 108. As shown in the figures, the body 108 may include markings 136 to indicate an amount of fluid drawn into the fluid receiving chamber 120. As shown, the body 108 includes 30 markings 136 numbered at 0.5 ml intervals, but any type of marking 136 indicating the varying fluid levels within the body 108 is sufficient.

As would be understood by those skilled in the art, the stopper 110 may be made from rubber, silicone or any other suitable resiliently deformable material. The stopper 110 preferably has a shape and outer diameter substantially matching a shape and inner diameter of the central channel 118 (in this case, cylindrical) so that, as the stopper 110 moves through the channel 118 fluid distal of the stopper 110 is formed distally through the channel 118. As would be understood by those skilled in the art, the materials of the stopper 110 and the body 108 are selected so that, although the stopper 110 is dimensioned to form a substantially fluid tight seal with an internal surface of the body 108, it remains slidable within the channel 118. The distal surface 122 of the stopper 110 may be any suitable shape, for example substantially planar, substantially conical or domed. The proximal surface 124 of the stopper is configured to connect to the plunger 112. In an exemplary embodiment, plunger 112 is integrally formed with the proximal surface 124 of the stopper 110. In another exemplary embodiment, plunger 112 is a separate element attached to the stopper 110 via a snap fit feature or any other known method.

The plunger 112 extends from a proximal end 138 to a distal end 140 attachable to the stopper 110 along a central plunger axis. The plunger 112 may, for example, be an elongated rod extending from the stopper 110 proximally past the proximal end of the body 108. The plunger 112 in this embodiment is configured with four longitudinal ribs 142. However, those skilled in the art will understand that any shape for the plunger may be selected including cylindrical or a different number of ribs 142, etc. The proximal portion of the plunger 112 in this embodiment includes a user contact portion 144 adapted to be contacted by a user during use. The user contact portion 144 may comprise a substantially disc shaped portion or flange 146 in a plane substantially perpendicular to the axis L along which the plunger 112 extends. It will be understood that the user contact portion 144 may be any desired shape but that the disc 146 provides an increased surface area for contact by, a thumb of a user than would a bare end of the plunger 112. The plunger 112 is configured to attach to the stopper 110 such that movement of the disc 146 moves the plunger 112 and, consequently, this moves the stopper 110 proximally and distally within the channel 118 to reduce or increase the volume of the fluid receiving chamber 120 to draw fluid into or expel fluid out of the fluid receiving chamber 120.

The swabbing element 106 comprises an elongated hollow shaft 148 and a swab 150. The shaft 148 in this embodiment is a cylindrical tube-like body having a lumen 152 extending therethrough from a proximal end 154 to an open distal end 156 although those skilled in the art will understand that a shaft of any shape may be used. The shaft 148 is preferably formed of a rigid material such as, for example, plastic, glass or metal. An exemplary shaft 148 may be formed as a thin-walled, structurally firm, plastic which, as would be understood by those skilled in the art, may be easily and inexpensively manufactured. The lumen 152 may have a diameter of, for example, 2 mm to 4 mm. In an exemplary embodiment, the shaft 148 is secured at the proximal end 154 to the stopper 110 and extends distally from the stopper 110, exiting the body 108 of the syringe 102 through the distal opening 130. In another exemplary embodiment, the shaft 148 may be releasably coupled to the stopper 110 permitting the shaft 148 to be separated from the stopper 110, e.g., by breaking the shaft 148 at a weakened portion thereof or at a connection between the shaft 148 and the stopper 110 via a distal force applied thereto. For example, the user may apply a distal force (i.e., pulling motion) to the shaft 148 such that, above a certain threshold, the shaft 148 breaks away from the stopper 110 and can be pulled out of the receiving chamber 120. An outer diameter of the shaft 148 is dimensioned to form a substantially fluid tight seal with an internal surface of the distal opening 130 while remaining slidable with respect to the internal surface of the distal opening 130. The length of the shaft 148 is dimensioned such that when the stopper 110 is drawn to its proximal-most position, the shaft 148 extends distally past the distal opening 130 into the housing 104. That is, the distal end 156 of the shaft 148 always extends at least partially out of the distal opening 130 such that the fluid tight seal between the shaft 148 and the distal opening 130 remains intact. A plurality of holes 158 formed along at least a portion of the proximal portion of the shaft 148 extend through a wall of the shaft 148 to the lumen 152 providing for communication between the lumen 152 and the fluid receiving chamber 120. The holes 158 in this embodiment are formed in a substantially helical pattern, distributed evenly around a circumference of the shaft 148. It is noted however, that holes 158 may be formed in any pattern or arrangement on the shaft 148 without deviating from the scope of the present embodiments. For example, in an alternate embodiment (not shown), the holes 158 may be situated only on a portion of the circumference of the shaft 148. The diameter of each of the holes 158 is selected to allow targeted specimens to flow therethrough. For example, the holes 158 may have a diameter of 2 mm to 3 mm. The holes 158 are located on a proximal portion of the shaft 148 such that when the stopper 110 and plunger 112 are in the distal-most position, the holes 158 remain within the syringe 102. Specifically, the holes 158 remain within the fluid receiving chamber 120 through an entire range of motion of the plunger 112 to prevent fluid from flowing out of the receiving chamber 120.

The swab 150 is secured to the distal end 156 of the shaft 148 such that it surrounds a distal opening 160 of the lumen 152. The swab 150 may be formed of any biocompatible, absorptive material such as, for example, cotton or a sponge material which is wound or secured around the distal open end of the shaft 148. The swab 150 may be attached to the shaft 148 via any known means such as, for example, an adhesive. In another example, the swab 150 may be a hollow cap that friction fits within or over the distal end 156 of the shaft 148.

The housing 104 of this embodiment extends from a proximal end 162 to an open distal end 164 along the central longitudinal axis L and, in this exemplary embodiment, is substantially cylindrical. The housing 104 may be formed of any suitable biocompatible material as would be understood by those skilled in the art. The housing 104 may, for example, be substantially rigid and includes a central channel 166 extending therethrough from the proximal end 162 to the distal end 164. The channel 166 is sized and shaped to slidably house the swabbing element 106 therein when the device 100 is in an insertion configuration as well as when the device is being withdrawn from the body. The proximal end 162 of the housing 104 is coupled to a distal end of the syringe body 108, with the nozzle 126 and the swabbing element 106 extending into the channel 166 of the housing 104. In an exemplary embodiment, the housing 104 is removably coupled to the syringe body 108, as shown in FIG. 5. In this embodiment, the housing 104 with the swabbing element 106 can be disconnected from the syringe 102 to preserve a swab culture therein for processing. The housing 104 has a length selected such that, when in the insertion configuration, the distal end of the swabbing element 106 (i.e., the swab 150) is fully contained within the housing 104 while, when in the extended configuration, the swabbing element 106 extends distally from the distal end 164 of the housing 104. In a preferred embodiment, the swabbing element 106 extends distally from the housing 104 by a distance selected so that, when in the extended configuration, the entire swab 150 projects distally from the housing 105. For example, the swabbing element 106 may extend distally beyond the distal end of the housing 104 by approximately 5 mm to 20 mm. However, those skilled in the art will understand that the housing 104 may be of any length depending on the requirements of the procedure to be performed. In an exemplary embodiment, the housing 104 includes a gel culture medium 168 on an inner surface thereof or embedded into the inner walls of the housing 104. In this embodiment, the housing 104 may be squeezed to break an enveloping shield, releasing the gel 168 to cover the swab 150 after it has drawn back into the housing 104. In an embodiment, the housing 104 may further include a housing cap 170 sized and shaped to fit over the distal end 164 of the housing 104 to prevent the cell culture and gel culture medium 168 from exiting the housing 104.

In an exemplary embodiment, the device 100 further includes a syringe cap 172. The syringe cap 172, similar to the housing cap 170, is configured to prevent fluid from escaping from the distal opening 130 of the syringe 102 after the housing 104 and the swabbing element 106 have been separated therefrom. The syringe cap 172 is sized and shaped to fit over the distal end of the nozzle 126. The syringe cap 172 may be formed in any shape so long as it forms a fluid-tight seal with the syringe 102 when it is placed on the nozzle 126.

In use, as shown in FIGS. 1-5, the fluid sampling device 100 of the present invention is inserted into a living body until a distal portion thereof is adjacent to target fluid to be sampled. During insertion, the swabbing element 106 may be held in a distal-most resting position with a distal end thereof seated in the opening at the distal end of the housing 104 to prevent non-targeted tissue from entering the shaft 148, as can be seen in FIG. 1. When the target fluid to be sampled has been reached, the swabbing element 106 is advanced distally to the extended configuration with the swab 150 projecting distally from the housing 150 into the target fluid to be sampled. The swab 150 may be maintained in this position until it is saturated with the fluid sample, as can be seen in FIG. 2. Specifically, the swabbing element 106 is driven distally relative to the housing 104 by distal movement of the plunger 112 to extend the swabbing element 106 beyond the distal end 164 of the housing 104 into contact with the target sample. As noted above, dimensions of the various elements of the device 100 may be selected so that the portion of the swabbing element 106 extending distally beyond the distal end 164 of the housing 104 has a desired length depending on the requirements of the procedure to be performed. The housing 104 and syringe 102 may then be sized accordingly, so that, when retracted, the swabbing element 106 is housed completely therein. As shown in FIG. 3, once the target are has been accessed by the swabbing element 106, a sample of the target fluid may be aspirated into the syringe by proximal movement of the plunger, applying a negative pressure to the lumen 152. This pressure draws the sample fluid through the holes 158 into the fluid receiving chamber 120. Drawing the plunger 112 proximally also draws the swabbing element 106 proximally such that the swab 150 is again housed within the housing 104 and the swab culture is embedded in the gel culture medium 168. After the sampling process has been completed, the device 100 is withdrawn proximally and removed from the body. The housing 104 and swabbing element 106 may then be disconnected from the syringe 102, as seen in FIGS. 4-5. Both the housing 104 and the syringe 102 may then be capped and transferred to appropriate tubes or media for processing.

It will be apparent to those skilled in the art that various modifications and variations may be made to the structure and methodology of the present invention without departing from the spirit or scope of the invention. Thus, the present invention covers all modifications and variations so long as they come within the scope of the appended claims and their equivalents.

What is claimed is:

1. A medical device, comprising:
a syringe including a syringe body defining a fluid receiving chamber and a plunger slidably received therein;
a hollow shaft extending distally from the plunger and exiting the syringe via a distal opening of the syringe, a proximal portion of the shaft including a first opening permitting fluid flow from a central lumen of the shaft to an exterior of the shaft, the first opening being located on the shaft so that the first opening remains within the syringe through an entire range of motion of the plunger, a distal end of the shaft being surrounded by an absorbent material; and
a hollow housing extending distally from the syringe and surrounding the shaft, the hollow housing being sized so that, when the plunger is withdrawn to a proximal-most position, the distal end of the shaft is received within the hollow housing and, when the plunger is advanced distally through the syringe, the distal end of the shaft is extended distally out of a distal end of the hollow housing.

2. The device of claim 1, further comprising an end cap removably coupled to the distal end of the hollow housing.

3. The device of claim 1, wherein the shaft includes a second opening located on the shaft, the second opening remaining within the syringe through the entire range of motion of the plunger.

4. The device of claim 1, wherein inner walls of the hollow housing are coated with a gel culture medium.

5. The device of claim 4, wherein applying a radially inward force to the hollow housing causes the inner walls of the hollow housing to contact the absorbent material such that the gel culture medium coats the absorbent material.

6. The device of claim 1, wherein the shaft and the distal opening of the syringe form a seal between the syringe and the hollow housing.

7. The device of claim 1, wherein the hollow housing is removably coupled to the syringe such that application of a predetermined force disconnects the hollow housing from the syringe.

8. The device of claim 7, further comprising a syringe cap removably coupled to the distal opening of the syringe.

9. A fluid sampling device, comprising:
a syringe including a syringe body defining a fluid receiving chamber;
a stopper slidably received within the syringe;
a plunger extending from a proximal end to a distal end, the proximal end of the plunger coupled to the stopper to slide the stopper relative to the housing;
a hollow shaft extending distally from the stopper and exiting the syringe via a distal opening of the syringe, a proximal portion of the shaft including a first opening permitting fluid to flow from a distal opening through a central lumen of the shaft and into the fluid receiving chamber, a distal end of the shaft being surrounded by an absorbent material; and
a hollow housing extending distally from the syringe and surrounding the shaft, the hollow housing being sized so that, when the plunger is withdrawn to a proximal-most position, the distal end of the shaft is received within the hollow housing and, when the plunger is advanced distally through the syringe, the distal end of the shaft is extended distally out of a distal end of the hollow housing.

10. The device of claim 9, wherein the first opening is located on the shaft so that the first opening remains within the syringe through an entire range of motion of the plunger.

11. The device of claim 9, wherein the shaft includes a second opening located on the shaft, the second opening remaining within the syringe through an entire range of motion of the plunger.

12. The device of claim 9, wherein inner walls of the hollow housing are coated with a gel culture.

13. The device of claim 12, wherein applying a radially inward force to the hollow housing causes the inner walls of the hollow housing to contact the absorbent material such that the gel culture medium coats the absorbent material.

14. The device of claim 9, wherein the hollow housing is removably coupled to the syringe such that application of a predetermined force disconnects the hollow housing from the syringe.

15. The device of claim 9, wherein the shaft is removably coupled to the stopper such that application of a predetermined force disconnects the shaft from the stopper.

16. A method for sampling fluid, comprising:
inserting a fluid sampling device into a body until a distal portion thereof is adjacent to a target fluid to be sampled, the fluid sampling device comprising:
a syringe including a syringe body defining a fluid receiving chamber and a plunger slidably received therein;
a hollow shaft extending distally from the plunger and exiting the syringe via a distal opening of the syringe, a proximal portion of the shaft including a first
opening permitting fluid flow from a central lumen of the shaft to an exterior of the shaft, the first opening being located on the shaft so that the first opening remains within the syringe through an entire range of motion of the plunger, a distal end of the shaft being surrounded by an absorbent material; and
a hollow housing extending distally from the syringe and surrounding the shaft, the hollow housing being sized so that, when the plunger is withdrawn to a proximal-most position, the distal end of the shaft is received within the hollow housing and, when the plunger is advanced distally through the syringe, the distal end of the shaft is extended distally out of a distal end of the hollow housing;

advancing the shaft distally out of the hollow housing, through distal movement of the plunger, such that the absorbent material contacts the target fluid;

drawing the shaft proximally into the hollow housing, through proximal movement of the plunger, so that the target fluid is drawn through the central lumen and into the fluid receiving chamber.

17. The method of claim 16, further comprising disconnecting the hollow housing from the syringe.

18. The method of claim 16, further comprising disconnecting the shaft from the plunger.

19. The method of claim 16, wherein the fluid sampling device further comprises an end cap removably coupled to the distal end of the hollow housing.

20. The method of claim 16, wherein the shaft and the distal opening of the syringe form a seal between the syringe and the hollow housing.

21. The method of claim 16, wherein inner walls of the hollow housing are coated with a gel culture medium.

22. The method of claim 21, further comprising:

applying a radially inward force to the hollow housing so the inner walls of the hollow housing contact the absorbent material so the gel culture coats the absorbent material.

* * * * *